United States Patent [19]

Larson et al.

[11] 4,233,025

[45] Nov. 11, 1980

[54] HOLLOW COTTON ROLL

[76] Inventors: William A. Larson, 1215 Paseo Dorado, Fullerton, Calif. 92631; Dale P. Wilterink, 1645 W. Cris Ave., Anaheim, Calif. 92802

[21] Appl. No.: 18,782

[22] Filed: Mar. 8, 1979

[51] Int. Cl.³ .................. A61C 5/14; A61C 17/04
[52] U.S. Cl. .................. 433/136; 433/91; 87/6; 128/276; 128/269
[58] Field of Search .................. 433/136, 138, 139, 91, 433/93, 94, 96; 87/6, 10; 128/276, 269, 270, 271, 296, 157, 156, 155

[56] References Cited

U.S. PATENT DOCUMENTS

| 480,471 | 8/1892 | Melotte | 433/136 |
| 525,797 | 9/1894 | Richmond | 128/269 |
| 1,210,720 | 1/1917 | Stephan | 128/269 |
| 1,742,080 | 12/1929 | Jones | 433/93 |
| 1,744,122 | 1/1930 | Keeling | 128/157 |
| 1,766,341 | 6/1930 | Kulik | 433/91 |
| 1,930,712 | 10/1933 | Girvin | 433/136 |
| 1,985,667 | 12/1934 | Nelson et al. | 433/136 |
| 2,644,234 | 7/1953 | Scott | 433/136 |
| 2,813,051 | 11/1957 | MacHenry | 128/296 |
| 3,203,418 | 8/1965 | Johnston | 128/269 |

FOREIGN PATENT DOCUMENTS 562059  10/1932  Fed. Rep. of Germany .......... 128/270

Primary Examiner—Louis G. Mancene
Assistant Examiner—John J. Wilson
Attorney, Agent, or Firm—Philip M. Hinderstein

[57] ABSTRACT

An elongate, generally cylindrical, hollow cotton roll for use with metal or plastic aspirators or suction tubes for keeping an area dry in medicine and dentistry. The roll has an inner layer of an open mesh fabric which receives the end of the aspirator, a layer of cotton or synthetic roving surrounding the fabric layer, and a layer of braided yarn surrounding the roving to retain same. Also disclosed is a machine for manufacturing such a cotton roll in a continuous length.

16 Claims, 11 Drawing Figures

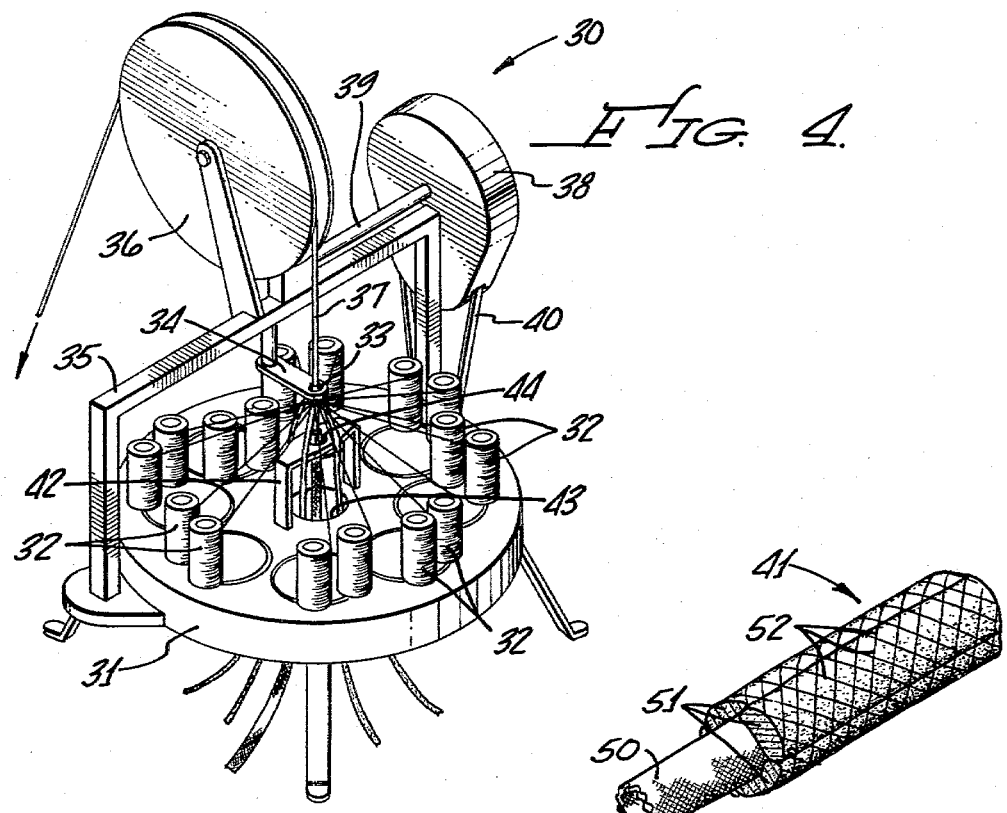
FIG. 4.
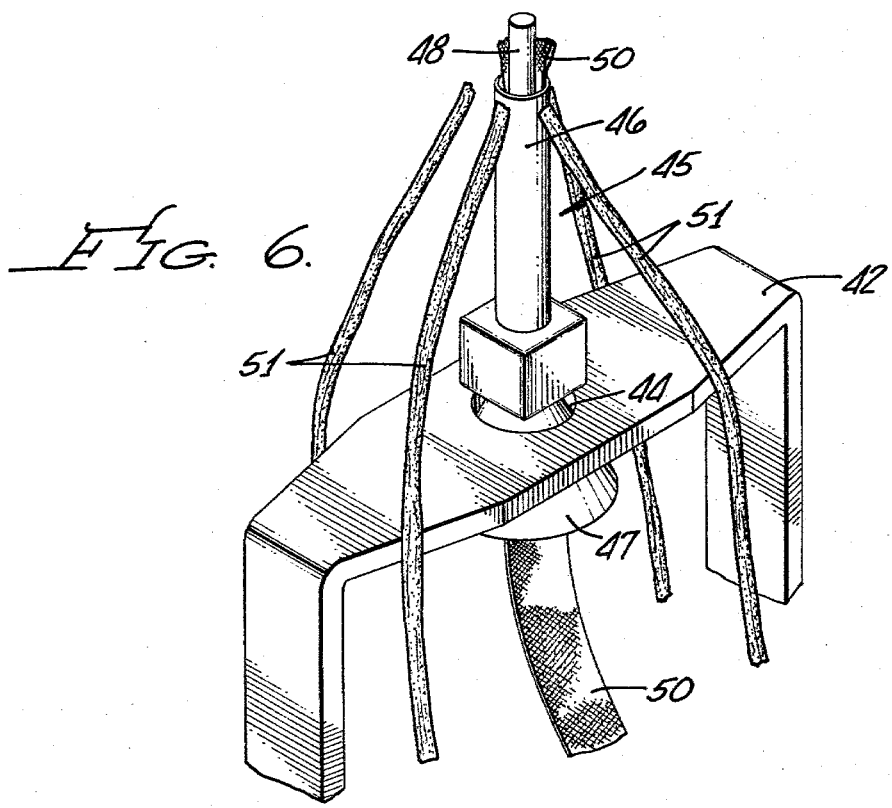
FIG. 5.
FIG. 6.

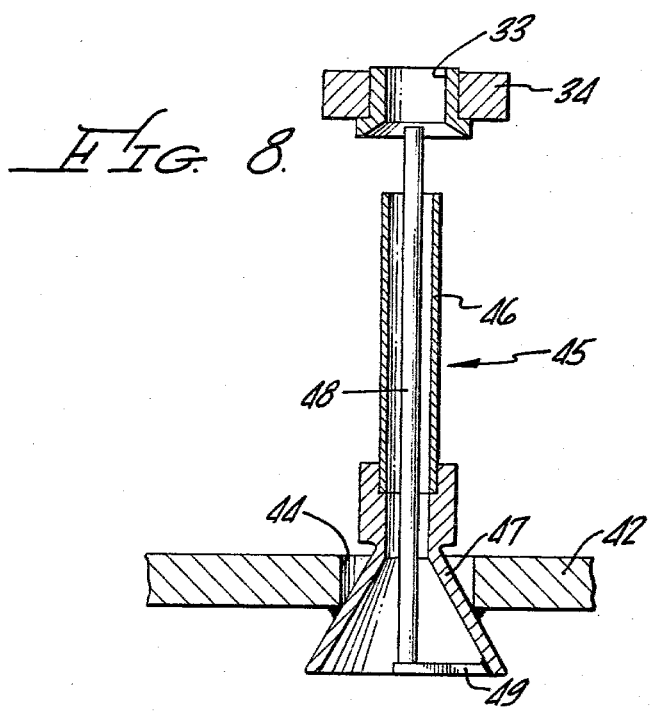
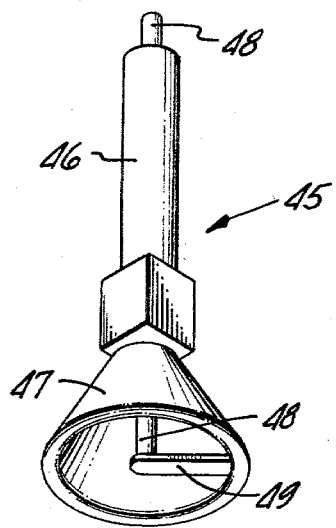
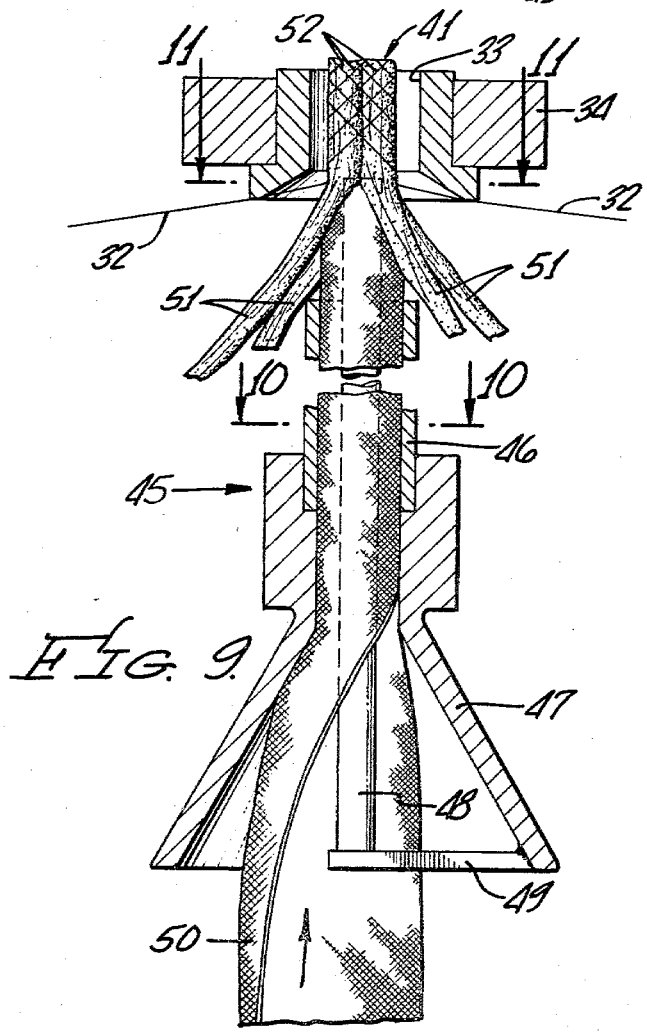
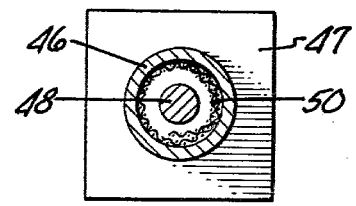
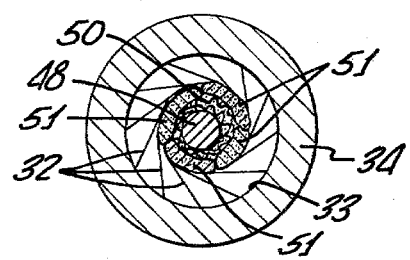

HOLLOW COTTON ROLL

BACKGROUND OF THE INVENTION

1. Field of the Invention

The present invention relates to a hollow absorbent roll for use with an aspirator and, more particularly, to an elongate, generally cylindrical, hollow cotton roll for solving aspiration problems in medicine and dentistry in surgical and irrigation procedures.

2. Description of the Prior Art

In the field of dentistry, it is known that mucous and solid debris accumulate within the mouth of a patient during various procedures. Because it is both a nuisance and time-consuming to terminate the dental procedure while the patient himself expels the mucous and solid debris, it is common for dentists to use a variety of methods to absorb and/or remove these substances. That is, it is common to use strips or rolls of cotton or other absorbent materials or sponges, which rolls or sponges are placed in the patient's mouth during the procedure. However, these rolls and sponges must be frequently changed.

Alternatively, or in addition to the cotton rolls and sponges, aspirators are used. Such aspirators are typically made of metal or plastic, including a hook-shaped member, one end of which is inserted in the mouth and the other end of which is connected to a source of suction. This permits a continuous evacuation of the mucous and other solid debris from the patient's mouth.

While an aspirator significantly improves the aspiration procedures in dentistry, problems still remain. There are still a number of times when cotton rolls are used, which rolls must be frequently changed. The metal aspirator typically sits on the floor of a patient's mouth so that suction is not always gentle, the suction being applied directly to the tissues on the inside of the mouth. This is often uncomfortable for the patient. To prevent this discomfort, a chairside assistant is usually needed to handle the aspirator so as to move it from place to place to insure continuous absorption of the mucous and other solid debris in the patient's mouth.

While the above discussion has been limited to the field of dentistry, it will be obvious that similar problems exist in other fields of medicine where there are related irrigation procedures, such as in surgery. That is, in a variety of surgical procedures, aspirators or suction tubes are used to remove blood, mucous, and irrigation solutions. In these procedures, many of the same problems exist, i.e. the need for frequent changes of cotton rolls, the need for an assistant, and the problem of suction on loose tissue.

SUMMARY OF THE INVENTION

According to the present invention, the aspiration problems in medicine and dentistry in surgical and irrigation procedures are solved by the provision of a hollow absorbent roll for use with an aspirator. That is, the above-described problems encountered in both medicine and dentistry are solved by fitting a hollow absorbent roll over the end of a metal or plastic aspirator or suction tube. The present hollow absorbent roll readily receives the end of an aspirator or suction tube and permits suction from the inside of the roll. This eliminates frequent changes of conventional solid cotton rolls. Furthermore, suction is gentle, without the suction of loose tissue as with conventional aspirators. When the present hollow cotton roll is applied over an aspirator, significantly greater patient comfort results over that encountered heretofore. Furthermore, a chairside assistant is not needed to handle the aspirator since it may be placed in a comfortable location and kept there during the medical or dental procedure.

Briefly, the present invention comprises an elongate, generally cylindrical, hollow absorbent roll for use with an aspirator including a layer of an open mesh fabric, such as gauze stiffened with starch, defining an inner wall of the roll, the aspirator being insertable within the fabric, a layer of an absorbent material, such as cotton or a synthetic fabric, surrounding the open mesh fabric, and a layer of braided yard surrounding the absorbent material to retain same, the entire roll being sized by spraying with a non-toxic, water-resistant starch. Such roll may be supplied in cut lengths or continuous lengths.

OBJECTS, FEATURES AND ADVANTAGES

It is therefore an object of the present invention to solve the aspiration problems encountered in medicine and dentistry in surgical and irrigation procedures. It is a feature of the present invention to solve these problems by the provision of a hollow absorbent roll for use with an aspirator. An advantage to be derived is the elimination of frequent changes of conventional, solid, absorbent rolls. A further advantage is that the suction now produced by an aspirator is more gentle than that encountered heretofore. A still further advantage is that patient comfort is increased. Another advantage is that chairside assistants are often not needed to handle an aspirator.

Still other objects, features, and attendant advantages of the present invention will become apparent to those skilled in the art from a reading of the following detailed description of the preferred embodiment constructed in accordance therewith, taken in conjunction with the accompanying drawings wherein like numerals designate like parts in the several figures and wherein:

BRIEF DESCRIPTION OF THE DRAWINGS

FIG. 4 is a perspective view of a conventional braiding machine modified to form a continuous length of absorbent roll;

FIG. 5 is a perspective view of a continuous length of absorbent roll manufactured by the machine of FIG. 1;

FIG. 6 is a perspective view of the attachment to the machine of FIG. 4 in accordance with the present invention;

FIG. 7 is a perspective view of a portion of the attachment of FIG. 6;

FIG. 8 is a sectional view of a portion of the attachment of FIG. 6;

FIG. 9 is an enlarged view of the attachment of FIG. 8 showing its operation; and FIGS. 10 and 11 are sectional views taken along the lines 10—10 and 11—11, respectively, in FIG. 9.

DESCRIPTION OF THE PREFERRED EMBODIMENT

Figure 1:
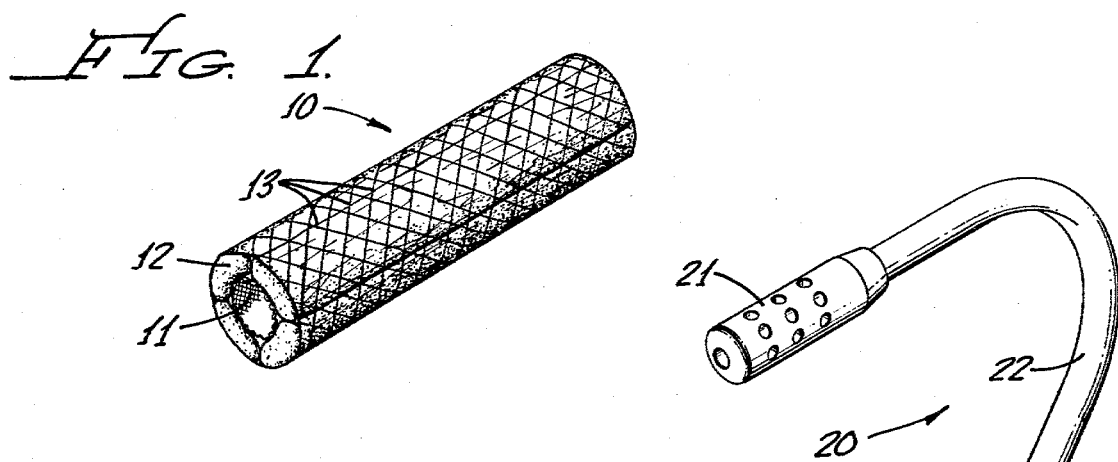
FIG. 1 is a perspective view of a hollow absorbent roll constructed in accordance with the teachings of the present invention.
Figure 2:
FIG. 2 is a perspective view of a conventional dental aspirator.
Figure 3:
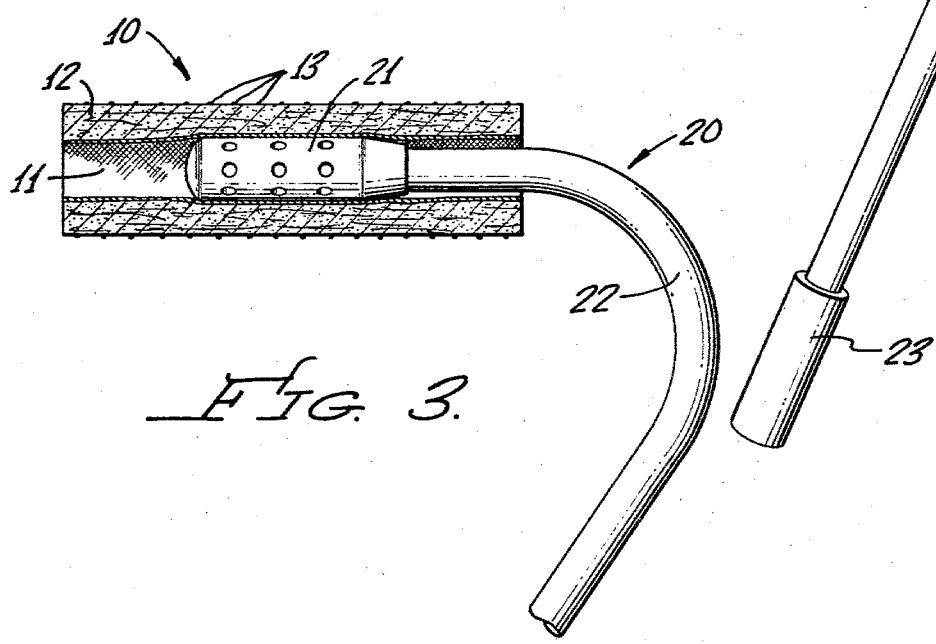
FIG. 3 is a sectional view showing the cotton roll of FIG. 1 in position on the aspirator of FIG. 2.

Referring now to the drawings and, more particularly, to FIGS. 1-3 thereof, there is shown a hollow absorbent roll 10 constructed in accordance with the present invention for use, for example, with a conventinal dental aspirator 20. Absorbent roll 10 is an elongate, generally cylindrical, hollow member having three separate layers. More specifically, hollow roll 10 includes a layer 11 of an open mesh fabric defining the inner wall of the hollow chamber. Layer 11 is preferably formed from cotton or a synthetic fabric, typically gauze, sized (stiffened) with a non-toxic water-resistant starch. In this manner, layer 11 retains its shape forming a channel for receipt of the end 21 of aspirator 20. As is know in the art, aspirator 20 includes a hook-shaped body 22 having end 21 at one end thereof, the other end 23 thereof being adapted to be connected to a source of suction.

Surrounding gauze layer 11 is a layer 12 of an absorbent material which absorbs the mucous and solid debris or other fluids during use of roll 10. Layer 12 may be pharmaceutical cotton, or rayon, or a synthetic roving.

Surrounding absorbent layer 12 is a layer of braided or woven yarn 13 which functions to retain absorbent layer 12 and to insure that roll 10 maintains its shape. To further insure against flaring or fraying of roll 10, the outside thereof may be sized with a non-toxic, water-resistant resin paste or starch. This can conveniently be done by spraying roll 10 after completion of the manufacturing operation.

In use, roll 10 may be supplied in either cut lengths, as shown in FIG. 1, or in continuous lengths to be cut to size when ready to use. In a dental procedure, roll 10 is inserted over end 21 of aspirator 20 and inserted with aspirator 20 into the mouth of a patient. The absorbent material of layer 12 continuously draws mucous and solid debris threinto where it is continuously removed by aspirator 20.

Referring now to FIGS. 4–11, absorbent roll 10 may be manufactured on a conventional braiding machine, generally designated 30, of a type well known to those skilled in the art, for use in manufacturing shoelaces, drawcords for garments, and many other braided fabrics. Such a braiding machine 30 includes a table 31 on which is supported a plurality of rolls of yarn 32. As is known to those skilled in the art, table 31 and yarn rolls 32 turn to form a continuous braiding pattern, the individual lengths of yarn extending through an opening 33 in an arm 34 connected to a bracket 35. Bracket 35 supports a drive wheel 36, the braided yarn 37 extending over wheel 36. The entire machine operation is controlled by a motor (not shown) mounted within a housing 38, the motor being connected to wheel 36 by a shaft 39 and being connected to table 31 and yarn rolls 32 by a belt drive 40.

Braiding machine 30, as just described, is a conventional machine modified as described hereinafter for manufacturing absorbent roll 10 in a continuous length, as shown at 41. More specifically, braiding machine 30 is modified to include an inverted U-shaped bracket 42 mounted above a central opening 43 in table 31. Bracket 42 has a central opening 44 aligned with opening 43 for supporting a forming member, generally designated 45. Forming member 45 includes an elongate sleeve 46, one end of which is connected to the apex of a cone-shaped member 47 which extends through opening 44 in bracket 42, the larger diameter end of cone-shaped member 47 extending beneath bracket 42. A shaft 48 extends through cone-shaped member 47 and sleeve 46, shaft 48 being supported at its lower end by an arm 49 connected to member 47. The upper end of shaft 48 extends into opening 33 in arm 34 whereas the upper end of sleeve 46 is spaced from arm 34.

The operation of forming member 45 may be best understood with reference to FIGS. 6, 9, 10, and 11. Layer 11 of open mesh fabric is provided as a continuous strip 50 of gauze which is fed through opening 43 in table 31 and into the open base of cone-shaped member 47, surrounding shaft 48. Cone-shaped member 47 directs gauze strip 50 towards the apex thereof and into sleeve 46, simultaneously forming the flat strip into a cylindrical strip, again as shown in FIG. 9. The cylindrical strip of gauze 50 then extends up through sleeve 46, between sleeve 46 and shaft 48, the combination of sleeve 46 and shaft 48 insuring the formation of gauze strip 50 into a cylindrical shape.

Layer 12 of absorbent material is preferably formed by feeding to braiding machine 30 multiple continuous strips 51 of cotton or synthetic roving. These strips 51 of roving may also extend through opening 43 in table 31, around bracket 42 and forming member 45. The individual strips of roving 51 are directed into opening 33 in arm 34, as shown most clearly in FIG. 9. At this point, shaft 48 is still retaining gauze strip 50 in its cylindrical shape, but the outside thereof has been exposed to roving strips 51 because shaft 48 extends beyond the end of sleeve 46. Therefore, the remainder of braiding machine 30 can operate in a conventional manner with yarn rolls 32 operating to form a layer of braided yarn 52 around the strips of cotton roving 51. The inclusion of shaft 48 at this point in the operation insures that the braiding machine does not collapse roving 51 and gauze strip 50. In any event, the completed length of absorbent roll 41 extends through opening 33 in arm 34 and is pulled therethrough by drive wheel 36. The completed assembly may be directed to a spraying station and then to a storage roller or cutting machine, as desired.

It can therefore be seen that according to the present invention, the aspiration problems in medicine and dentistry in surgical and irrigation procedures are solved by the provision of a hollow absorbent roll 10 for use with an aspirator 20. That is, the previously described problems encountered in both medicine and dentistry are solved by fitting a hollow absorbent roll 10 over the end 21 of a metal or plastic aspirator or suction tube 20. Hollow absorbent roll 10 readily receives end 21 of aspirator 20 and permits suction from the inside thereof. This eliminates frequent changes of conventional solid cotton rolls. Furthermore, suction is gentle, without the suction of loose tissue as with conventional aspirators. When a hollow cotton roll 10 is applied over an aspirator, significantly greater patient comfort results over that encountered heretofore. Furthermore, a chairside assistant is often not needed to handle aspirator 20 since it may be placed in a comfortable location and kept there during the medical or dental procedure.

While the invention has been described with respect to the preferred physical embodiment constructed in accordance therewith, it will be apparent to those skilled in the art that various modifications and improvements may be made without departing from the scope and spirit of the invention. Accordingly, it is to be understood that the invention is not to be limited by the specific illustrative embodiment, but only by the scope of the appended claims.

We claim:

1. An elongate, generally cylindrical, hollow absorbent roll for use with an aspirator comprising:
   a layer of an open mesh fabric defining an inner wall of said roll, said aspirator being insertable within said fabric;
   a layer of an absorbent material surrounding said fabric layer; and
   a layer of braided yarn surrounding said absorbent material to retain same.

2. An absorbent roll according to claim 1, wherein said open mesh fabric is gauze.

3. An absorbent roll according to claim 2, wherein said gauze is stiffened with starch.

4. An absorbent roll according to claim 1, wherein said inner wall is of cotton or a synthetic fabric.

5. An absorbent roll according to claim 1, 2, 3, or 4, wherein said absorbent material is cotton or synthetic roving.

6. An absorbent roll according to claim 5, wherein said braided yarn is of cotton or a synthetic material.

7. An absorbent roll according to claim 1, 2, 3, or 4, wherein said yarn is of cotton or a synthetic material.

8. An absorbent roll according to claim 1, wherein said absorbent roll is sized with a non-toxic, water-resistant starch.

9. A method of making an elongate, generally cylindrical, hollow absorbent roll for use with an aspirator comprising the steps of:
   providing a continuous strip of an open mesh fabric;
   forming said open mesh fabric strip into a generally cylindrical shape;
   surrounding said open mesh fabric strip with a continuous length of absorbent material; and
   continuously forming a layer of braided yarn around said absorbent strip.

10. A method according to claim 9, wherein said open mesh fabric is gauze.

11. A method according to claim 10, wherein said gauze is stiffened with starch.

12. A method according to claim 9, wherein said open mesh fabric is of cotton or a synthetic material.

13. A method according to claim 9, 10, 11, or 12, wherein said absorbent material is cotton or synthetic roving.

14. A method according to claim 13, wherein said braided yarn is of cotton or a synthetic material.

15. A method according to claim 9, 10, 11, or 12, wherein said yarn is of cotton or a synthetic material.

16. A method according to claim 9, further comprising the step of:
   sizing said roll with a non-toxic, water-resistant starch.

* * * * *